(12) United States Patent
Miskiel et al.

(10) Patent No.: US 8,363,876 B2
(45) Date of Patent: Jan. 29, 2013

(54) AUDIOMETRIC DEVICES

(75) Inventors: Edward Miskiel, Miami, FL (US); Rafael E. Delgado, Coral Gables, FL (US); Juan Carlos Bordo, Miami, FL (US); Beverly Gail Lim, Boca Raton, FL (US)

(73) Assignee: Mednax Services, Inc., Sunrise, FL (US)

( * ) Notice: Subject to any disclaimer, the term of this patent is extended or adjusted under 35 U.S.C. 154(b) by 916 days.

(21) Appl. No.: 12/334,770

(22) Filed: Dec. 15, 2008

(65) Prior Publication Data

US 2009/0190786 A1 Jul. 30, 2009

Related U.S. Application Data

(60) Provisional application No. 61/013,673, filed on Dec. 14, 2007, provisional application No. 61/013,678, filed on Dec. 14, 2007.

(51) Int. Cl.
*H04R 25/00* (2006.01)

(52) U.S. Cl. ............ 381/380; 381/60; 381/72; 381/322; 381/370; 381/371; 381/372

(58) Field of Classification Search .................. 381/380, 381/60, 72, 322, 370, 371, 372
See application file for complete search history.

(56) References Cited

U.S. PATENT DOCUMENTS

| | | | | | |
|---|---|---|---|---|---|
| 4,029,083 | A | * | 6/1977 | Baylor | 600/559 |
| 4,048,444 | A | * | 9/1977 | Giampapa | 381/67 |
| 4,156,118 | A | * | 5/1979 | Hargrave | 381/372 |
| 4,616,643 | A | * | 10/1986 | Jung | 128/866 |
| 4,781,196 | A | * | 11/1988 | Killion | 600/379 |
| 4,807,688 | A | * | 2/1989 | Beetle | 164/72 |
| 4,870,688 | A | * | 9/1989 | Voroba et al. | 381/60 |
| 4,930,520 | A | * | 6/1990 | Liverani | 600/559 |
| 5,201,007 | A | * | 4/1993 | Ward et al. | 381/328 |
| 5,243,709 | A | | 9/1993 | Sheehan et al. | |
| 5,405,822 | A | * | 4/1995 | Landgrebe et al. | 503/227 |
| 5,826,582 | A | | 10/1998 | Sheehan et al. | |
| 5,828,757 | A | * | 10/1998 | Michalsen et al. | 381/328 |
| 5,913,309 | A | | 6/1999 | Sheehan et al. | |
| 6,386,314 | B1 | | 5/2002 | Sheehan et al. | |
| 6,390,970 | B1 | * | 5/2002 | Muller | 600/25 |
| D469,873 | S | | 2/2003 | Warring et al. | |
| 6,832,663 | B2 | | 12/2004 | Warring et al. | |
| 2002/0058881 | A1 | | 5/2002 | Raviv et al. | |
| 2002/0080988 | A1 | | 6/2002 | Raviv | |
| 2004/0216947 | A1 | * | 11/2004 | Warring et al. | 181/129 |
| 2005/0157899 | A1 | * | 7/2005 | Raviv et al. | 381/322 |
| 2007/0003086 | A1 | * | 1/2007 | Tilson et al. | 381/328 |
| 2008/0002848 | A1 | * | 1/2008 | Heerlein et al. | 381/328 |
| 2009/0316921 | A1 | * | 12/2009 | Lloyd et al. | 381/60 |
| 2010/0185115 | A1 | | 7/2010 | Causevic et al. | |

OTHER PUBLICATIONS

Algo, "Newborn Hearing Screening Supplies," 2 pages, unknown date.
Bio-Logic Systems, Inc, "Halo Ear Muffin from Bio-logic," 2004, 6 pages, unknown date.
Etymotic Research, Inc., "ER-3A Insert Headphones for Audiometry," 4 pages.
Viasys Neurocare, "Auditory & ENG Electrodes & Accessories," 1 page, unknown date.

\* cited by examiner

*Primary Examiner* — A. Sefer
(74) *Attorney, Agent, or Firm* — Brenda Herschbach Jarrell; Paul A. Nuzzi; Choate, Hall & Stewart LLP (57) ABSTRACT

A method includes adhering an audiometric device to a surface of an ear or to an ear canal, the audiometric device including an adhesive contacting the surface of the ear or the ear canal; and conducting an audiometric procedure with the audiometric device adhered to the surface of the ear or the ear canal.

7 Claims, 10 Drawing Sheets

AUDIOMETRIC DEVICES

CROSS-REFERENCE TO RELATED APPLICATIONS

This application claims priority to U.S. Provisional Patent Applications 61/013,673 and 61/013,678, both filed on Dec. 14, 2007, and entitled "Ear Coupling Device For Audiometric Testing," hereby incorporated by reference in their entirety.

TECHNICAL FIELD

The invention relates to audiometric devices and related methods.

BACKGROUND

Audiometric tests are used for performing hearing screening, comprehensive diagnostic assessment, and audiological research. Audiometric testing systems provide a means to elicit and acquire signals evoked in response to appropriate auditory stimuli. Some common audiometric testing systems are: behavioral audiometry; auditory evoked potentials (AEPs) that include auditory brainstem responses (ABRs); and auditory steady state responses (ASSRs), and otoacoustic emissions (OAEs).

Three common types of sound-delivery devices for audiometric testing are headphones, insert earphones, and ear probes. Each of these sound-delivery devices has a coupling interface with the patient's ear during testing. This coupling interface is responsible for delivering a sound stimulus to the ear, as well as providing a seal to the ear to reduce ambient background noise that might interact with the delivered stimulus and influence measurements. These coupling interfaces may be an integral part of the sound-delivery device (as in the case of headphones) or offered as optional accessories (as in the case of eartips for insert earphones and ear probes).

Audiometric headphones include both over-the-external-ear ("circumaural") and on-the-external-ear ("supra-aural") varieties. These devices contain both the sound-transducer device circuitry as well as the coupling interface/cushion used to deliver the sound stimulus to the patient. In the case of circumaural headphones, the coupling interface is provided by ear "cups" that fully enclose the entire external ear (similar to full-sized headphones used to listen to music). This interface creates a fully-closed seal that provides acoustic isolation to effectively block out any ambient background noise and minimize leakage of sound to the outside environment, as well as providing enhanced sound quality and improved low-frequency response performance. In the case of supra-aural headphones, the coupling interface is provided by ear "pads" that are applied on the ear (similar to the relatively compact, ear pad headphones used to listen to music). Since these pads rest on the outer ear, the coupling interface is not fully sealed, and therefore this interface may offer poor background noise exclusion and inferior interaural (i.e., between the ears) attenuation. Typical materials used to manufacture the ear cups and pads of the headphones include polyurethane foam, silicone, various rubbers, and elastomers. Both circumaural and supra-aural headphones are comfortable to wear, easy to apply, and require no special training to use since no object is inserted into the patient's ear canal. However, these headphones can cause interference with earrings, glasses, and hairstyles, and cause unwanted electromagnetic interference near the ear. Also, since they typically do not contain any disposable components, the earphone cushions and headbands may need cleaning to be sanitary.

Audiometric insert earphones and ear probes are intra-aural (in the ear) devices that perform the same intended function as audiometric headphones, except a small end piece is inserted into the ear canal. This insertion can provide an effective seal that provides isolation from external noise. Both insert earphones and ear probes are compact and lightweight, and due to their small sizes, there is little to no interference with earrings, glasses, hairstyles, etc. Audiometric insert earphones typically includes an isolated transducer case (that houses the sound transducer device circuitry) and a hollow tubing that connects to an adaptor/eartip to convey the stimulus signal from the sound transducer to the patient's ear. Ear probes, on the other hand, combine both the transducer circuitry and transmission tubing into one casing. Both audiometric insert earphones and ear probes are coupled to the patient's ear by means of disposable or reusable accessories to deliver the sound stimulus. These accessories have been classified by some manufacturers as "earphone cushions" that come in two varieties: eartips and/or ear cups.

Eartips are small "plugs" that connect to the sound output ends of audiometric earphones and ear probes and are inserted into the patient's ear canal to provide a coupling interface between the earphone or ear probe and the ear. Since the patient's ear canal is fully sealed, eartips can provide effective background noise reduction and increased interaural attenuation. These plugs are typically made of polyurethane foam, silicone, or various elastomers, and come in a variety of shapes and sizes suitable for both adult and infant testing. They are typically single-use, disposable devices, and do not require high overall maintenance. An appropriate insertion depth (fit) is used for a proper seal and ambient sound attenuation.

An ear cup is an alternative sound-delivery device accessory used with some audiometric testing systems. Ear cups offer a compromise between the coupling interfaces for audiometric headphones and earphones or ear probes, by providing an additional intermediary interface between the earphone or ear probe and the ear. Like eartips, ear cups attach to the sound output end of an earphone or ear probe (using the stimulator's own tip, a separate eartip, or an adaptor). Like headphone cushions, ear cups are placed over the entire external ear during audiometric testing, without inserting an eartip into the patient's ear canal. Since the ear cup covers the entire ear, it can provide an effective seal against background noise and offer good interaural attenuation. Ear cups are typically disposable, thus requiring no maintenance, are comfortable to wear, are easy to apply, and do not require much training to use since there is no insertion into the patient's ear canal. Typical materials used to manufacture ear cups include polyurethane foam, silicone, and various elastomers. The portion of the device that makes skin contact with the patient is a thin layer of adhesive, such as a skin contact adhesive or hydrogel, used to adhere the device onto the skin of the patient's head.

SUMMARY

In one aspect, the invention features a method including adhering an audiometric device to a surface of an ear or to an ear canal, the audiometric device including an adhesive contacting the surface of the ear or the ear canal; and conducting an audiometric procedure with the audiometric device adhered to the surface of the ear or the ear canal.

Embodiments may include one or more of the following features. The audiometric device is adhered to the surface of the ear (e.g., only to the surface of the ear). The audiometric device is adhered to the ear canal (e.g., only to the ear canal).

The audiometric device is further adhered to a surface of a patient's head. The audiometric device does not contact a patient's head.

The audiometric device can be adhered to the surface of the ear, and the audiometric device can include a flexible body having a first side and a second side, an apertured portion extending from the first side, and the adhesive on the second side. The audiometric device can be further adhered to a patient's head. The flexible body can be generally circular. The flexible body and the apertured portion can include different compositions. The method can further include engaging a sound delivery device to the apertured portion.

The audiometric device can be adhered to the ear canal, the audiometric device can include a body including a channel and a first portion configured to be inserted into the ear canal, and the adhesive is on at least a portion of the first portion. The body can further include a second portion that is wider than the first portion, and the channel can extend through the first and second portions. The method can further include engaging a sound delivery device to the channel.

The audiometric device can be adhered to the surface of the ear, and the audiometric device can include an integrated sound delivery device. The adhesive can be on at least a portion of a toroidal portion of the audiometric device. The adhesive can be on at least a portion of a bell-shaped portion of the audiometric device. The audiometric device can include an inner portion configured to be insertable into the ear canal. The integrated sound delivery device can include a sound delivery tube, a wired speaker, or a wirelessly connected speaker.

In another aspect, the invention features an audiometric device including a flexible body shaped to substantially cover a patient's ear, the body having a first side and a second side; a first portion extending from the first side, the portion having an opening; and an adhesive on at least a portion of the second side.

Embodiments may include one or more of the following features. The flexible body is generally circular. The flexible body includes a tab (e.g., a tab that facilitates placement and/or removal of the device and that does not carry an adhesive). The first portion includes a protruding portion (e.g., a dome) extending away from the second side. The first portion and the flexible body include different compositions. The first portion is harder than the flexible body. The adhesive substantially covers the second side. The opening is constructed and arranged to allow a sound delivery device to engage with the opening and to delivery sound to an ear canal.

In another aspect, the invention features an audiometric device including a body having a channel extending through the body and sized to directly or indirectly receive a sound delivery device; and an adhesive carried by the body, wherein the audiometric device is sized and shaped to adhere to an ear canal.

Embodiments may include one or more of the following features. The body further includes an inner portion and an outer portion wider than the inner portion, and the channel extends through the inner and outer portions. The adhesive wholly or partially surrounds the inner portion. The adhesive and the inner portion are configured to be inserted into the ear canal.

In another aspect, the invention features an audiometric device including an inner portion configured to be inserted into an ear canal; an outer portion carrying an adhesive; and an integrated sound delivery device.

Embodiments may include one or more of the following features. The outer portion is bell-shaped. The outer portion is toroidal in shape. The integrated sound delivery device includes a sound delivery tube, a wired speaker, or a wirelessly connected speaker.

Embodiments may include one or more of the following features or advantages.

The audiometric devices can be used on patient of all ages comfortably and safely.

The audiometric devices can be easy to apply and to remove. For example, the devices can be biocompatible, non-sterile, single patient use, disposable devices. The devices can be used with different sound delivery devices.

Other aspects, features and advantages will be apparent from the description of the following embodiments and from the claims.

DETAILED DESCRIPTION

The invention relates to audiometric devices and related methods, e.g., methods of conducting an audiometric procedure. The audiometric devices can be placed on the ear or in the ear.

Figure 1A:
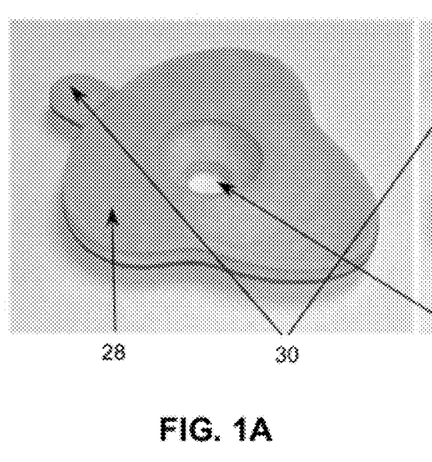
FIG. 1A is an inner view of an embodiment of an on-the-external-ear audiometric device.
Figure 1B:
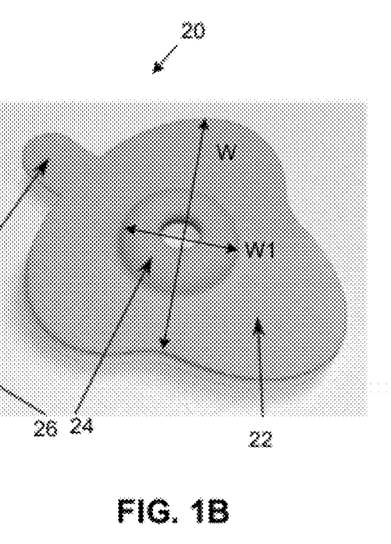
FIG. 1B is an outer view of the audiometric device shown in FIG. 1A.
Figure 2:
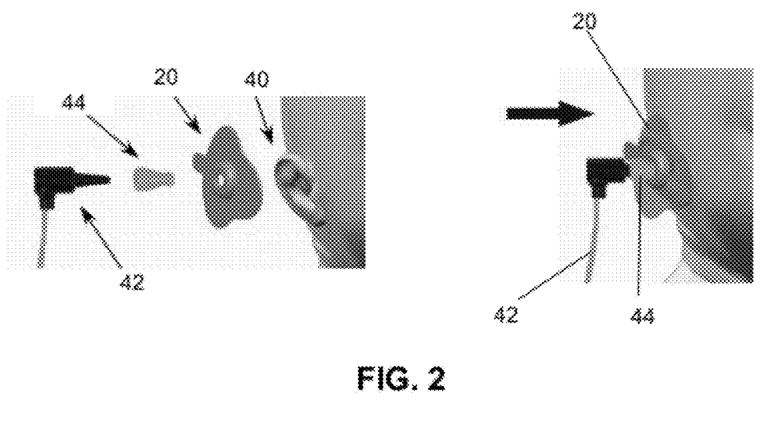
FIG. 2 is an illustration of an embodiment of a method of using the audiometric device shown in FIGS. 1A and 1B.

FIGS. 1A and 1B show an on-the-external-ear audiometric device 20 capable of acting as a coupling interface between a patient's ear and a sound delivery device that is used during audiometric testing. Briefly, device 20 includes a flexible body 22, a protruding portion 24 extending from the flexible body and having an aperture 26, and an adhesive 28 on the flexible body. Referring to FIG. 2, during use, device 20 covers a patient's ear 40 by adhering the device to the patient's ear by adhesive 28, and a sound delivery device 42 is inserted through aperture 26 to deliver sound to the ear.

Figure 3A:
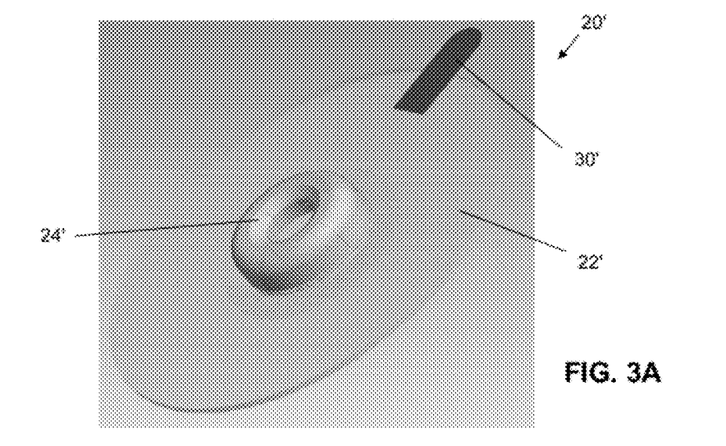
FIGS. 3A, 3B, and 3C are perspective views of an embodiment of an on-the-external-ear audiometric device.

Flexible body 22 is shaped and sized to cover (e.g., wholly cover) a patient's external ear. As shown in FIGS. 1A and 1B, flexible body 22 has an anisotropic, multi-lobe shape similar to an acorn that generally matches an ear and helps to align device 20 to the ear during use. But other shapes can be used. For example, referring to FIGS. 3A, 3B, and 3C, flexible body 22' can be substantially circular, so device 20' can be used without needing to position the device in a particular orientation. Other shapes include oval, elliptical, irregularly or regularly polygonal, and irregularly or regularly curvilinear. Similar to flexible body 22, flexible body 22' includes a protruding portion 24' and a removal tab 30'. Removal tabs 30, 30' are used to help remove devices 20, 20' after use (FIGS. 1A and 3A), but in other embodiments, no removal tab is included. Removal tabs 30, 30' can be formed unitarily with a flexible body (e.g., as shown in FIG. 1A) or as a separate component that is subsequently joined to a flexible body (e.g., as shown in FIG. 3A). A removal tab can be joined on an inner surface or an outer surface of a flexible body. The particular dimensions of body 22 depend on the intended use of device 20, e.g., whether the device will be used on an infant, a child, or an adult. The width and thickness of body 22 are selected to facilitate application and removal of device 20 to the intended patient, while also providing adequate coverage of the patient's ear and blockage of unwanted noise. In some embodiments, body 22 has an average width (W) from approximately 1.5 inch to approximately 2.5 inches. The average thickness of body 22 can range from approximately 0.01 inch to approximately 0.16 inch.

Flexible body 22 can include (e.g., be formed solely of) any flexible material that can be used for biomedical applications. Exemplary materials include resilient, hypoallergenic, non-irritating, and inert polymers, such as many thermoplastic elastomers. Specific examples of polymers include polyethylene (e.g., low density polyethylene), polyurethanes, silicones, rubbers (e.g., RIMFLEX®), polyolefin elastomers (e.g., ENGAGE™), and styrenic block copolymers (e.g., KRATON®).

Still referring to FIGS. 1A and 1B, apertured protruding portion 24 extends from an outer surface of flexible body 22 to an outer side of the flexible body (relative to the placement of device 20 during use). During use, protruding portion 24 and aperture 26 serve as a female connector for a sound delivery device, which is inserted through the aperture. As a result, protruding portion 24 is positioned such that when device 20 is properly adhered to the patient's ear, the sound delivery device can be inserted through aperture 26 to deliver sound to the ear canal. The particular dimensions of protruding portion 24 depend on the intended use of device 20 or the size of flexible body 22. The width and thickness of protruding portion 24 are selected to facilitate proper application, positioning, and removal of the sound delivery device to device 20, while also allowing the protruding portion to provide strain relief between the sound delivery device and device 20. In some embodiments, protruding portion 24 has an average width (W1) from approximately 0.45 inch to approximately 1.2 inch. The distance that protruding portion 24 extends from the outer surface of flexible body 22 can range from approximately 0.2 inch to approximately 0.5 inch. In some embodiments, the thickness of protruding portion 24 is greater than the thickness of flexible body 22, e.g., to facilitate insertion of sound delivery device 42 and to provide better strain relief. The average thickness of protruding portion 24 can range from approximately 0.21 inch to approximately 0.66 inch. Aperture 26 is sized to receive and to hold sound delivery device 42 directly or indirectly (e.g., via an intermediate adapter or an intermediate eartip). Aperture 26 can have an average width from approximately 0.2 inch to approximately 0.4 inch. Protruding portion 24 can have a variety of shapes, such as dome-like, toroidal (e.g., FIGS. 1A and 3A), cylindrical, frustro-conical, and convex.

Figure 3B:
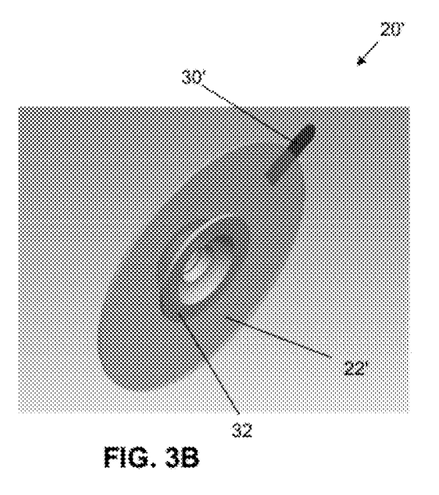
Figure 3C:
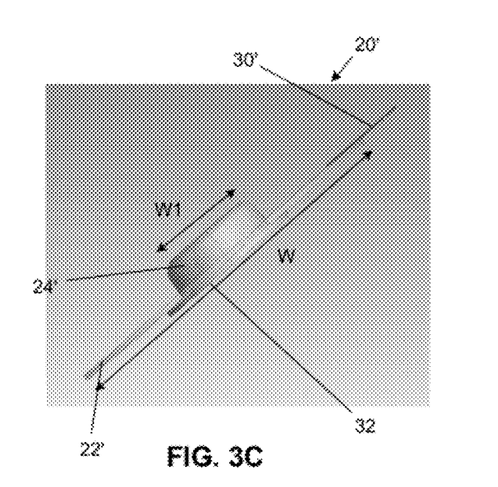
Figure 4A:
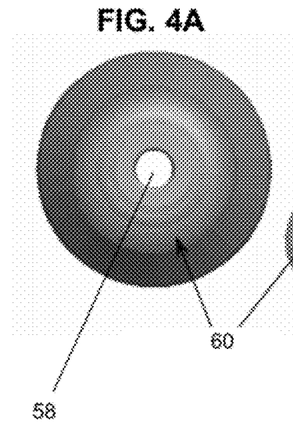
FIG. 4A is an inner view of an embodiment of an in-the-external-ear audiometric device.
Figures 4B, 4C:
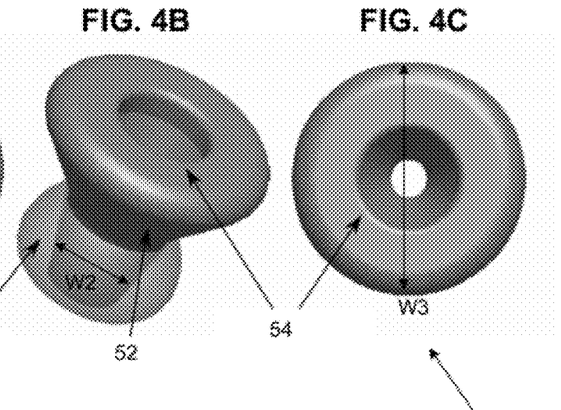
FIG. 4B is a perspective view of the audiometric device shown in FIG. 4A.
FIG. 4C is an outer view of the audiometric device shown in FIG. 4A.
Figure 4D:
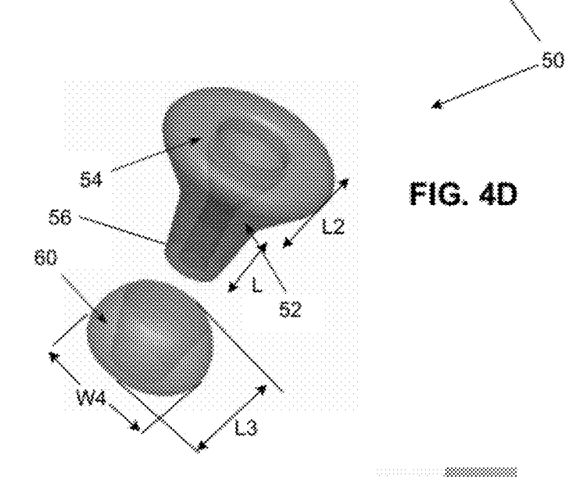
FIG. 4D is an exploded, perspective view of the audiometric device shown in FIG. 4A.

As shown, particularly in FIGS. 3A-3C, in some embodiments, protruding portion 24 is a separate component from flexible body 22 that is joined to the flexible body to form device 20. Forming protruding portion 24 as a separate component from flexible body 22 allows materials of different compositions and/or properties (e.g., hardness) to be used for each component. For example, flexible body 22 can be formed of a flexible material to provide comfort and conformability, while protruding portion 24 can be formed of a more rigid material to facilitate engagement with and positioning of the sound delivery device and to provide good strain relief. Examples of materials that can be included in protruding portion 24 include rubbers (e.g., RIMFLEX®), polyolefin elastomers (e.g., ENGAGE™), and styrenic block copolymers (e.g., KRATON™). As shown in FIGS. 3A-3C, one way to join protruding portion 24 to flexible body 22 is to form the protruding portion with a flange 32, and to form the flexible body with an opening sized to receive the protruding portion but not the flange. Protruding portion 24 and flexible body 22 can be joined by inserting the protruding portion through the opening until flange 32 contacts the inner side of the flexible body, and securing the protruding portion and the flexible body together with adhesive 28.

Adhesive 28 is used to secure device 20 to a patient's ear. As shown, adhesive 28 covers the entire surface area of the inner side of flexible body 22. In other embodiments, adhesive 28 covers at least approximately 30%, at least approximately 40%, at least approximately 50%, at least approximately 70%, at least approximately 80%, or at least approximately 90% of the surface area of the inner side of flexible body 22. Adhesive 28 can include (e.g., be formed solely of) any material capable of enhancing adhesion between flexible body 22 and a patient's ear. In some embodiments, adhesive 28 includes a hydrogel adhesive, e.g., a medical-grade hydrogel adhesive. The hydrogel can be hypoallergenic, non-irritating, water soluble, non-sensitizing, non-cytotoxic, non-staining, and/or non-gritty. Examples of hydrogel adhesives include the AG700 Series from AmGel Technologies (Fallbrook, Calif.) (e.g., the AG702, AG703 or AG704 gels), 7-9700 Soft Skin Adhesive from Dow Corning, and the 9980 Hydrogel Adhesive Tape from 3M (St. Paul, Minn.). Typically, adhesive 28 is covered by a protective backing that is removed to expose the adhesive just prior to applying device 20 to the ear.

FIG. 2 shows a method of using audiometric device 20. First, the protective backing is removed (e.g., peeled) from device 20 to expose adhesive 28. Aperture 26 is located over (e.g., aligned with) the ear canal to facilitate transfer of sound into the ear canal, while device 20 is placed onto patient's ear 40 with adhesive 28 contacting the outer edges of the ear to create a seal. Slight pressure can be applied to device 20 to secure it to ear 40 and form a good conforming seal. In some embodiments, adhesive 28 does not contact the patient's head after device 20 is secured to ear 40. In other embodiments, a portion of device 20 (e.g., adhesive 28) contacts the patient's head, such as when the device is larger than the patient's ear. Next, sound delivery device 42 is connected to device 20 by inserting the sound delivery device through aperture 26 and into the ear canal. As shown in FIG. 2, sound delivery device 42 engages with audiometric device 20 via a disposable adapter 44, but in other embodiments, the sound delivery device can directly engage with the audiometric device with its own tip and without an intermediate device. In some embodiments, the tip of sound delivery device 42 (or the tip of an intermediate adapter) extends approximately 0 inch to approximately 0.15 inch past aperture 26. Once firmly placed, sound delivery device 42 can be activated and used to conduct an audiometric procedure (e.g., testing). After the procedure is done, sound delivery device 42 is disconnected from audiometric device 20, and the audiometric device can be removed from ear 42, e.g., using removal tab 30 or flexible body 22. Device 20' can be used similarly to device 20.

Referring now to FIGS. 4A, 4B, 4C, and 4D, an in-the-ear audiometric device 50 is shown. Device 50 includes a plug-shaped body 52 having an outer portion 54, an inner portion 56, and a channel 58 that extends through the entire length of the inner and outer portions. Device 50 further includes an adhesive 60 that surrounds at least a portion of (e.g., wholly) inner portion 56. Briefly, during use, referring to FIG. 5, device 50 is inserted into a patient's ear 62 such that outer portion 54 is positioned within the pinna of the ear, and inner portion 56 and adhesive 60 are positioned in the ear canal. A sound delivery device 62 is inserted into channel 58 and secured to audiometric device 50 to deliver sound to the ear canal.

Plug-shaped body 52 is configured to be placed within the pinna of the ear and in the ear canal. As shown, inner portion 56 is tapered to facilitate its insertion into the ear canal, and sized to fit in the ear canal. The inner end of inner portion 56 is narrower than the outer end of the inner portion. The particular dimensions of device 50 depend on its intended use, e.g., intended patient. In some embodiments, the average width (W2) or diameter of inner portion 56 ranges from approximately 0.10 inch to approximately 0.12 inch. The length (L1) of inner portion 56 can range from approximately 0.23 inch to approximately 0.28 inch. Juxtaposed to inner portion 56, outer portion 54 is wider than the inner portion and is also tapered to facilitate placement of audiometric device 50 within the pinna of the ear. The wider, outer end of outer portion 54 can also serve as a stop to limit insertion of audiometric device 50. In some embodiments, the average width (W3) or diameter of outer portion 54 ranges from approximately 0.6 inch to approximately 1.0 inch. The length (L2) of outer portion 54 can range from approximately 0.3 inch to approximately 0.5 inch. The entire length of plug-shaped body 52 can range from approximately 0.53 inch to approximately 0.78 inch. Channel 58 is configured to receive and to hold sound delivery device 64, and to direct sound to the ear canal. As shown, channel 58 has a funnel shape with a tapered portion and a non-tapered portion, but in other embodiments, other channel shapes (such as entirely tapered or entirely non-tapered) can be used. In some embodiments, the average width or diameter of channel 58 ranges from approximately 0.3 inch to approximately 0.1 inch. Plug-shaped body 52 can include (e.g., be formed solely of) a polymer, such as a thermoplastic elastomer (e.g., KRATON®, RIMFLEX®, ENGAGE™).

Adhesive 60 includes a channel 66 (as shown, a tapered channel) to receive inner portion 56 so that the adhesive can be attached to plug-shaped body 52. Adhesive 60 is sized and shaped to fit within the ear canal with inner portion 56. In some embodiments, adhesive 60 has an average outer width (W4) or diameter of from approximately 0.4 inch to approximately 0.6 inch. The length (L3) of adhesive 60 can range from approximately 0.23 inch to approximately 0.28 inch. Adhesive 60 can have a curved profile (as shown) or other profiles (e.g., a linear, non-tapered profile) that facilitate insertion of the adhesive and inner portion 56 into the ear canal. Adhesive 60 can include (e.g., be formed solely of) the same materials as adhesive 28 described above that are covered by a protective backing.

Figure 5:
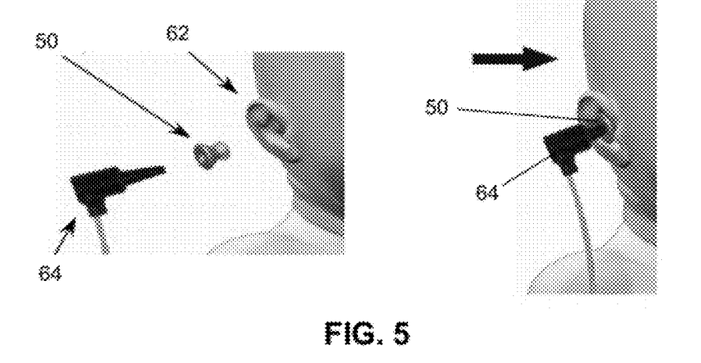
FIG. 5 is an illustration of an embodiment of a method of using the audiometric device shown in FIGS. 4A-4D.

In use, referring to FIG. 5, the protective backing is removed (e.g., peeled) from audiometric device 50 to expose adhesive 60, and the device is placed in and on ear 62. More specifically, once properly positioned, inner portion 56 of plug-shaped body 52 and adhesive 60 are in the ear canal, and outer portion 54 of the plug-shaped body is within the pinna of the ear. Adhesive 60 only contacts the ear canal. Slight pressure can be applied to audiometric device 50 to secure it to ear 62 and form a good seal. Next, sound delivery device 64 is connected to audiometric device 50 by inserting the sound delivery device into channel 58 of plug-shaped body 52. As shown in FIG. 5, sound delivery device 64 directly engages with audiometric device 50 with its own tip and without an intermediate device, but in other embodiments, the sound delivery device engages with the audiometric device via an intermediate component, such as a disposable adapter or an eartip. Once securely engaged with audiometric device 50, sound delivery device 64 can be activated and used to conduct an audiometric procedure (e.g., testing). After the procedure is done, sound delivery device 64 is disconnected from audiometric device 50, and the audiometric device is removed from ear 62.

Figures 6A, 6B, 6C:
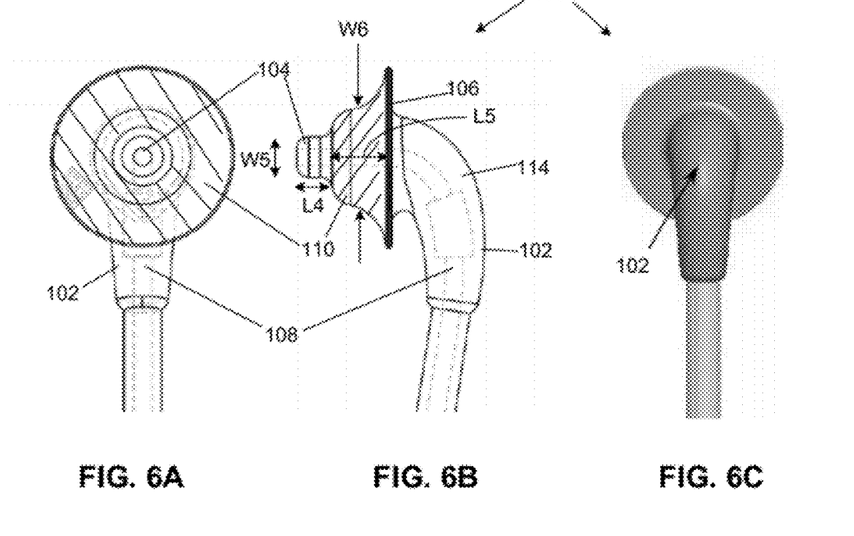
FIG. 6A is an inner view of an embodiment of an in-the-external-ear audiometric device.
FIG. 6B is a side view of the audiometric device shown in FIG. 6A.
FIG. 6C is an outer view of the audiometric device shown in FIG. 6A.

Turning now to FIGS. 6A, 6B, and 6C, in some embodiments, an audiometric device and a sound delivery device are integrated. Audiometric device 100 includes a body 102 having an inner portion 104 and an outer portion 106, and a sound delivery device 108 in the body. Audiometric device 100 further includes an adhesive 110 on at least a portion of (e.g., wholly on) outer portion 106. Briefly, referring to FIG. 7, during use, audiometric device 100 is inserted into a patient's ear 112 such that adhesive 110 is positioned within the pinna of the ear, and inner portion 104 is positioned in the ear canal.

Inner portion 104 and outer portion 106 are configured to be placed within the pinna of the ear and in the ear canal, respectively. As shown, inner portion 104 has a nipple-like shape that is generally cylindrical and rounded at its inner end to facilitate insertion of the inner portion into the ear canal. Inner portion 104 is sized to fit in the ear canal. The particular dimensions of device 100 depend on its intended use, e.g., intended patient. In some embodiments, the average width (W5) or diameter of inner portion 104 ranges from approximately 0.1 inch to approximately 0.4 inch. The length (L4) of inner portion 104 can range from approximately 0.1 inch to approximately 0.2 inch. Juxtaposed to inner portion 104, outer portion 106 is wider than the inner portion and has a bell-shaped profile that allows the outer portion to be placed within the pinna of the ear. The wider, outer end of outer portion 106 can also serve as a stop to limit insertion of audiometric device 100. In some embodiments, the average width (W6) or diameter of outer portion 106 ranges from approximately 0.5 inch to approximately 1.5 inches. The length (L5) of outer portion 106 can range from approximately 0.15 inch to approximately 0.25 inch. As shown, juxtaposed to the outer end of outer portion 106, body 102 further includes a downwardly-extending portion 114. Body 102 can include (e.g., be formed solely of) a polymer, such as a thermoplastic elastomer (e.g., KRATON®, RIMFLEX®, ENGAGE™).

Adhesive 110 is sized and shaped to fit within the pinna of the ear with outer portion 106. Adhesive 110 can include (e.g., be formed solely of) the same materials as adhesive 28 described above that are covered by a protective backing.

Other configurations for outer portion 106 and adhesive 110 can be used. For example, referring to FIGS. 8A, 8B, 8C, and 9, outer portion 106' has a toroidal shape that allows the outer portion and adhesive 110 to be placed within the pinna of the ear. In some embodiments, the average outer width (W7) or diameter of outer portion 106' ranges from approximately 0.4 inches to approximately 0.8 inches. The length (L6) of outer portion 106' can range from approximately 0.15 inches to approximately 0.25 inches. Other shapes for outer portion 106 and adhesive 110 include frustro-conical.

Located within body 102, sound delivery device 108 can include any device capable of delivering sound to inner portion 104 and ear 112. For example, body 102 can be hollow and contain a sound delivery tube. As other examples, sound delivery device 108 can include a speaker that is battery-powered, or wired or wirelessly connected to a controller and/or a power source that sends a signal to the speaker to produce a sound.

Figure 7:
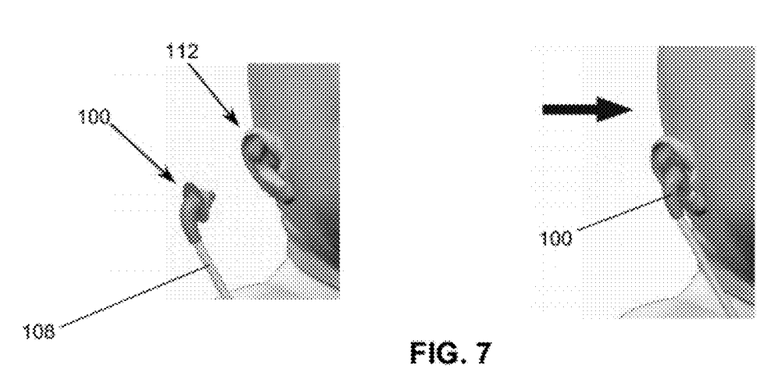
FIG. 7 is an illustration of an embodiment of a method of using the audiometric device shown in FIGS. 6A-6C.
Figures 8A, 8B, 8C, 9:
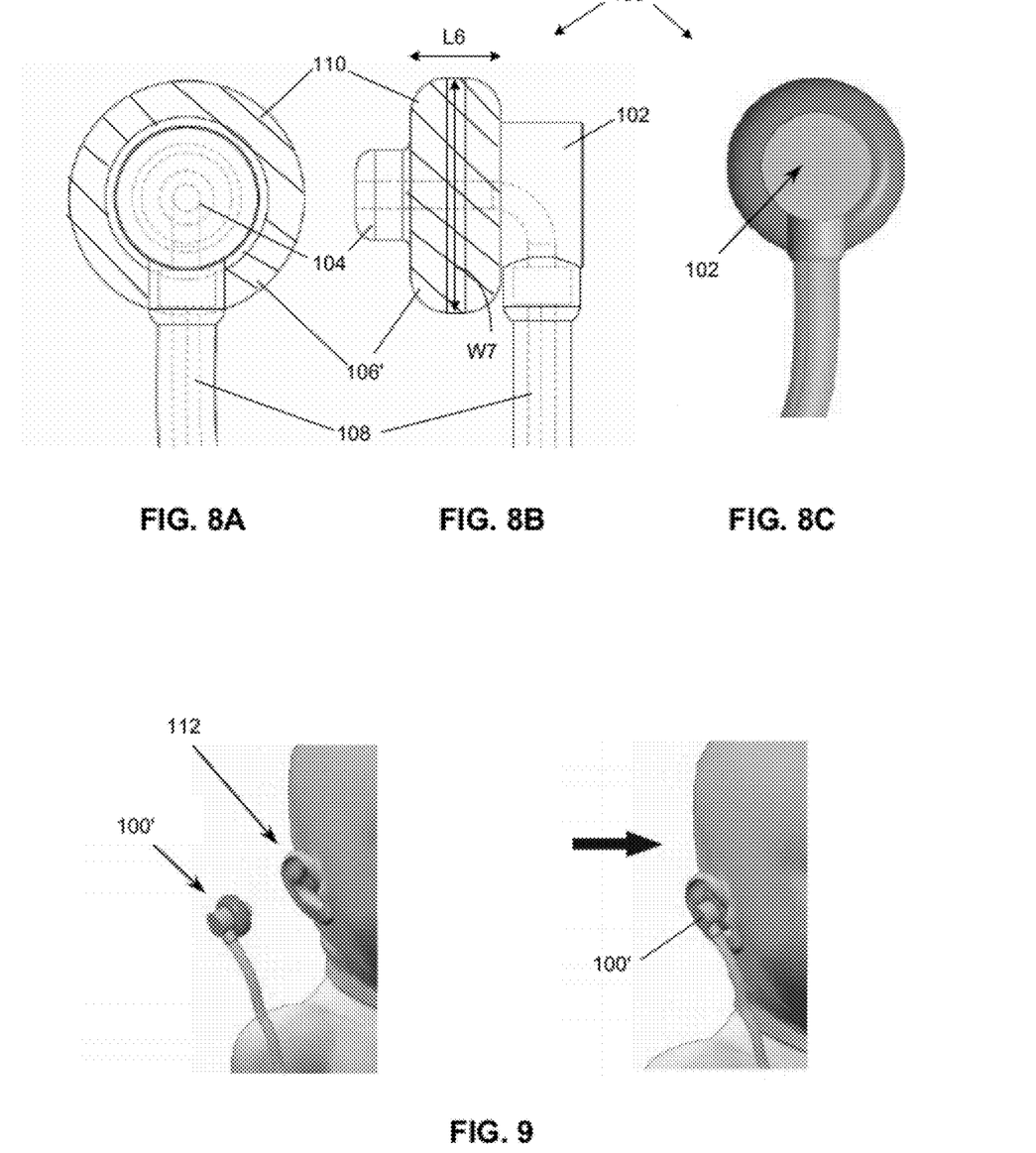
FIG. 8A is an inner view of an embodiment of an in-the-external-ear audiometric device.
FIG. 8B is a side view of the audiometric device shown in FIG. 8A.
FIG. 8C is an outer view of the audiometric device shown in FIG. 8A.
FIG. 9 is an illustration of an embodiment of a method of using the audiometric device shown in FIGS. 8A-8C.

In use, referring to FIGS. 7 and 9, the protective backing is removed (e.g., peeled) from audiometric device 100 to expose adhesive 110, and the device is placed in and on ear 112. More specifically, inner portion 104 of body 102 is in the ear canal, and outer portion 106 and adhesive 110 are within the pinna of the ear. Adhesive 110 only contacts the pinna of the ear. Slight pressure can be applied to audiometric device 100 to secure it to ear 112 and form a good seal. After audiometric device 100 is securely engaged with ear 112, sound delivery device 108 can be activated and used to conduct an audiometric procedure (e.g., testing). After the procedure is done, audiometric device 100 is removed from ear 62. Audiometric device 100' is used similarly to audiometric device 100.

While a number of embodiments have been described, the invention is not so limited.

For example, audiometric devices 20, 20', 50 can be unitarily formed with (e.g., irremovable from) a sound delivery device. Audiometric devices 20, 20', 50 can be cleaned (e.g., sterilized) after use and/or prior to re-use.

Protruding portion 24, 24' and flexible body 22, 22' can be formed as a unitary, one-piece component.

Device 20, 20' can include one or more layers between flexible body 22, 22' and adhesive 28. For example, the layer(s) can include a material that enhance adhesion between the flexible body and the adhesive, e.g., when the adhesive does not bond sufficiently with a selected material for the flexible body.

Figure 18:
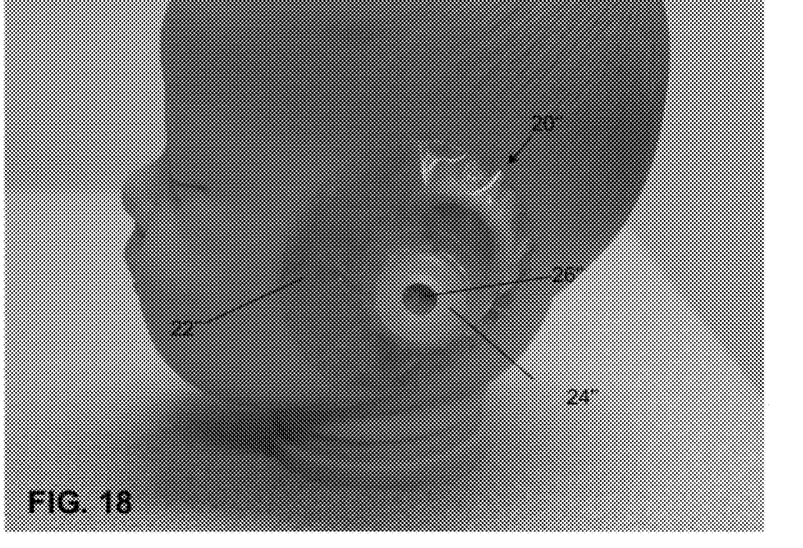
FIGS. 18 and 19 show an embodiment of an audiometric device and a method of using the same.
Figure 19:
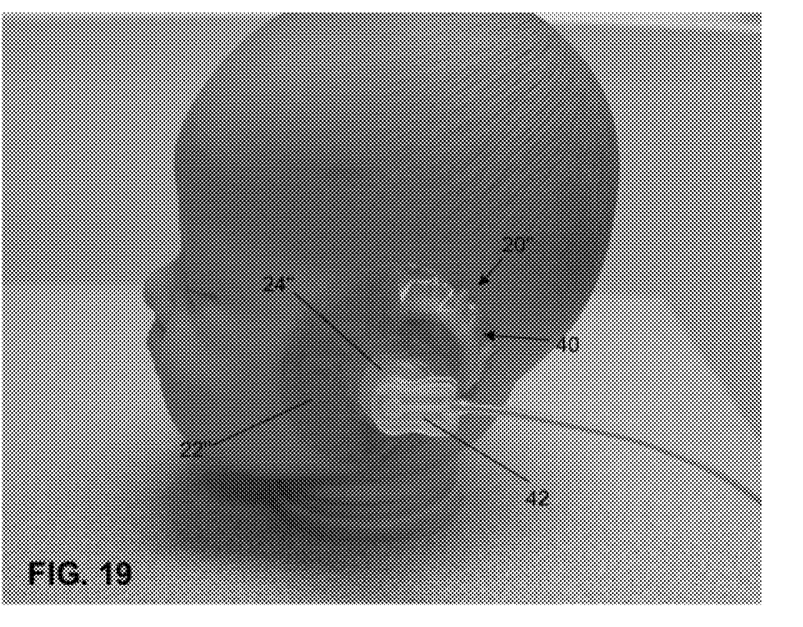

As indicated above, in some embodiments, an on-the-ear audiometric device contacts both a patient's ear and the patient's head. FIGS. 18 and 19 show an audiometric device 20" including a flexible body 22", a protruding portion 24" with an opening 26" on an outer side of the flexible body, and an adhesive (not visible) on an inner side of the flexible body. Device 20" is similar to device 20 described above. When device 20" adhered to the patient's ear 40 via the adhesive during use, the device (e.g., the adhesive) also contacts and adheres to the patient's head, at areas surrounding the ear. As shown, flexible body 22" completely covers and envelops ear 40, so the flexible body can be made very thin to allow it to conform well around and over ear 40. Sound delivery device 42 is inserted through opening 26" to deliver sound to ear 40.

The following Examples are illustrative and not intended to be limiting.

In the following Examples, sample auditory brainstem response (ABR) recordings were acquired from a single test subject stimulated with an Etymotic Research ER3A Earphone sound stimulator (refer to FDA number K930003), using different methods for coupling the stimulator to the subject's ear: (a) a standard foam insert eartip (manufactured by Etymotic Research) connected to the earphone tip and inserted into subject's ear canal; (b) the audiometric device shown in FIGS. 1A and 1B connected to the earphone (via a standard foam eartip) and placed onto the subject's ear (Example 1); and (c) the audiometric device shown in FIGS. 4A-4D connected to the earphone (via a standard foam eartip) and placed into the subject's ear (Example 2).

For each Example, the same test subject and acquisition system was used in both types of recordings. The acquisition system used to acquire these recordings was an Intelligent Hearing Systems' SMART-EP Auditory Evoked Potential System (refer to FDA number K904926). The system test parameters shown in Table 1 were used in all ABR recordings:

TABLE 1

| Parameter | Value |
| --- | --- |
| Stimulus | Click |
| Rate | 21.10 Hz |
| Sweeps | 1024 (averaged) |
| Filters | 100-1500 Hz |
| Intensity | 80 dB HL |
| Mode | Alternating Polarity |
| Gain | 100 |

Each ABR measurement was performed twice (i.e., two trials). There was a high level of repeatability in both trials of each set of recordings. The mean of the recordings were also calculated for the two trials using each ear-coupling method. This data is given in graphical format in FIGS. 10-17.

As shown, analysis of the recordings show that the audiometric devices described above are comparable to a common inserted foam eartip coupling method for ABR trace quality. For example, there is much similarity in the shapes and trace quality of the ABR recordings. There is also a large degree of agreement and matching between the amplitudes and latencies of various peaks in the recordings.

Example 1

Figure 10:
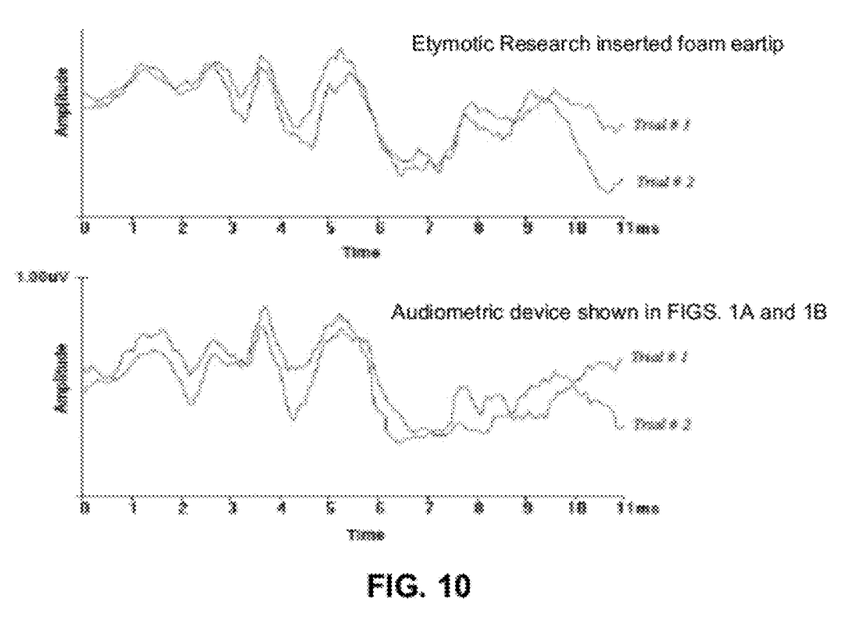
FIG. 10 shows sample auditory brainstem response (ABR) recordings acquired using an earphone sound stimulator with both an inserted foam eartip (Etymotic Research) (first graph) and the audiometric device shown in FIGS. 1A and 1B (second graph).
Figure 11:
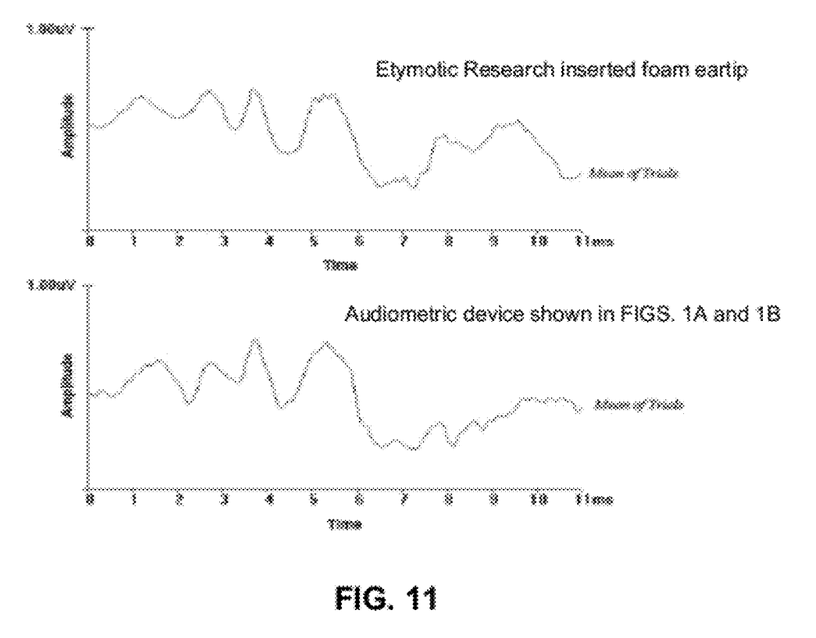
FIG. 11 shows the mean of two trials of sample ABR recordings acquired using an earphone sound stimulator with both an inserted foam eartip (Etymotic Research) (first graph) and the audiometric device shown in FIGS. 1A and 1B (second graph).
Figure 12:
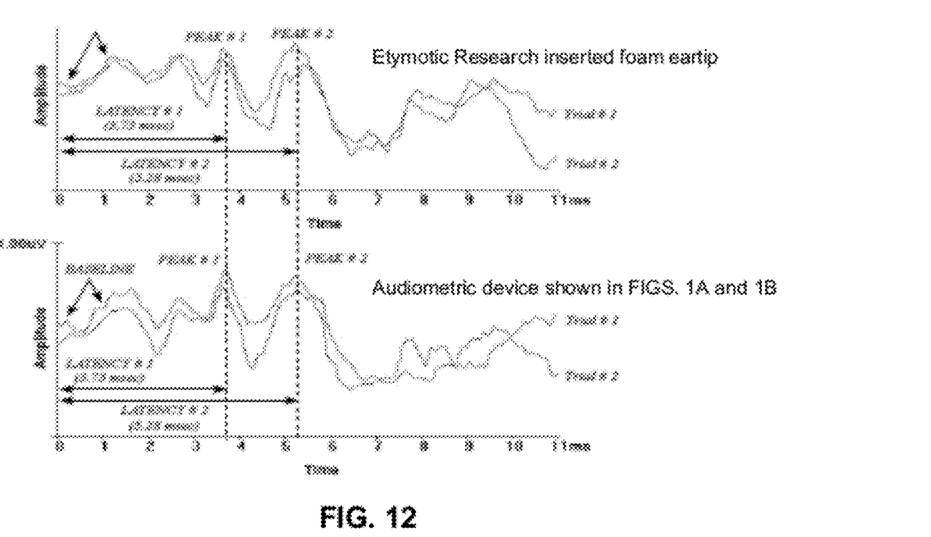
FIG. 12 shows sample ABR recordings acquired using an earphone sound stimulator with both an inserted foam eartip (Etymotic Research) (first graph) and the audiometric device shown in FIGS. 1A and 1B (second graph), with some measured time and amplitude parameter values (peaks, latencies, and baseline) marked.
Figure 13:
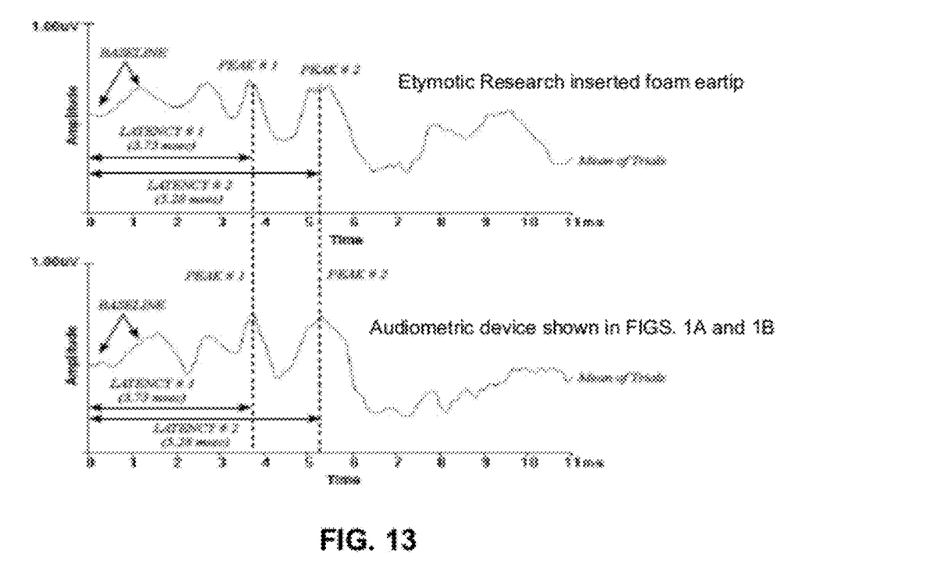
FIG. 13 shows the mean of the two trials of sample ABR recordings acquired using both an inserted foam eartip (Etymotic Research) (first graph) and the audiometric device shown in FIGS. 1A and 1B (second graph), with some measured time & amplitude parameter values (peaks, latencies, and baseline) marked.

FIG. 10 displays graphs of the sample ABR recordings acquired using the earphone sound stimulator with both a common inserted foam eartip (shown in the top graph) and the audiometric device of FIGS. 1A and 1B (shown in the bottom graph). Both sets of recordings show a high level of repeatability in the resulting acquired waveforms for each trial. FIG. 11 displays the mean of the two sets of ABR recordings for each type of ear coupling device used. There is much similarity in the shapes of both sets of these calculated mean ABR recordings. FIG. 12 displays the two sets of ABR recordings for each type of ear coupling device used along with some measured time and amplitude parameter values marked (as shown, peaks, latencies, and baseline). FIG. 13 displays the mean of the ABR recordings with the same measured time and amplitude parameter values marked. These graphs show that there is a large degree of agreement and matching between the amplitudes and latencies of various peaks of the recordings.

Example 2

Analysis of these recordings show that the audiometric device described above is comparable to the standard inserted foam eartip coupling method for ABR trace quality.

Figure 14:
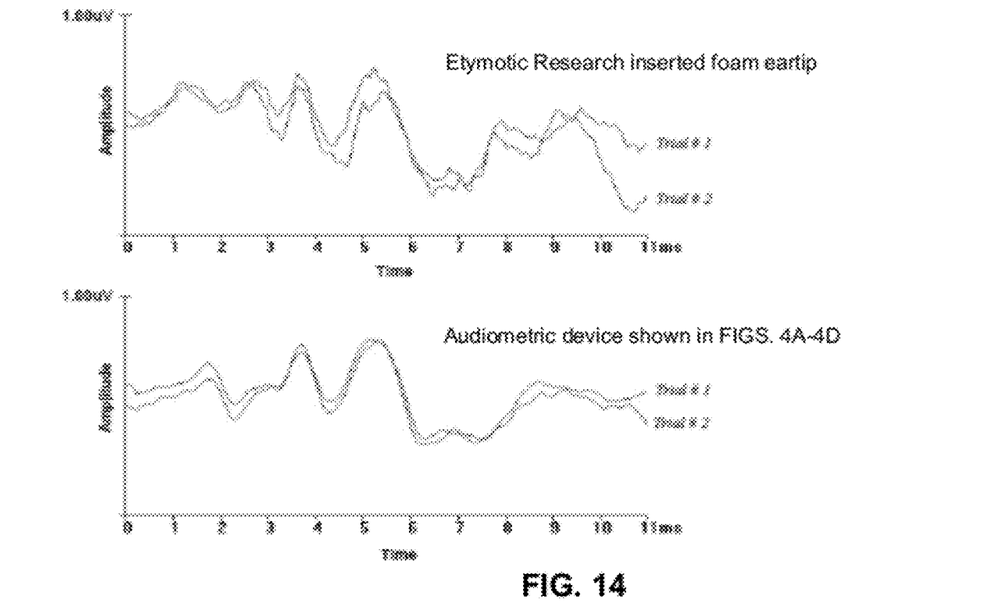
FIG. 14 shows sample ABR recordings acquired using an earphone sound stimulator with both an inserted foam eartip (Etymotic Research) (first graph) and the audiometric device shown in FIGS. 4A-4D (second graph).
Figure 15:
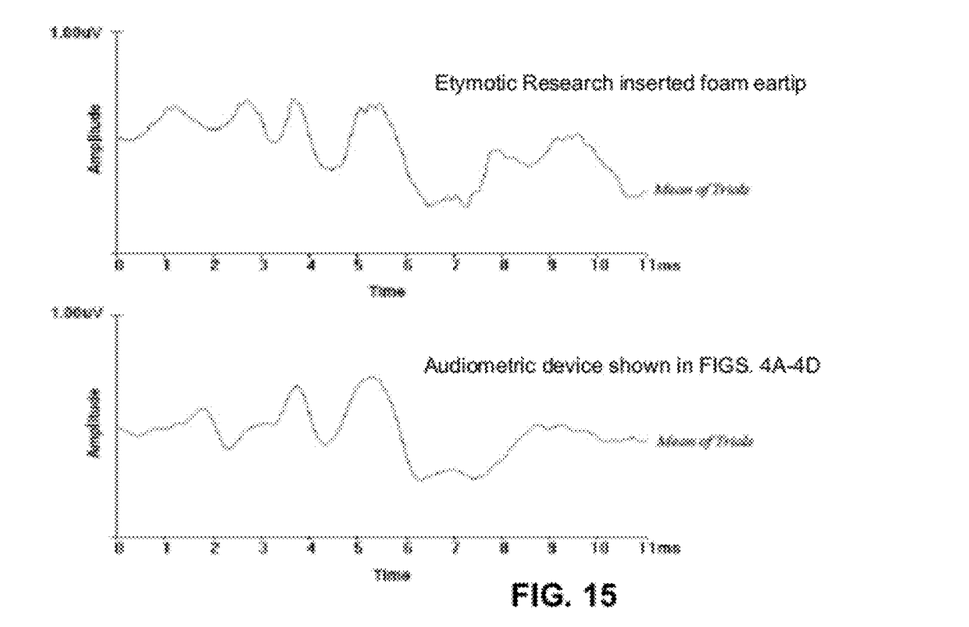
FIG. 15 shows the mean of the two trials of sample ABR recordings acquired using an earphone sound stimulator with both an inserted foam eartip (Etymotic Research) (first graph) and the audiometric device shown in FIGS. 4A-4D (second graph).
Figure 16:
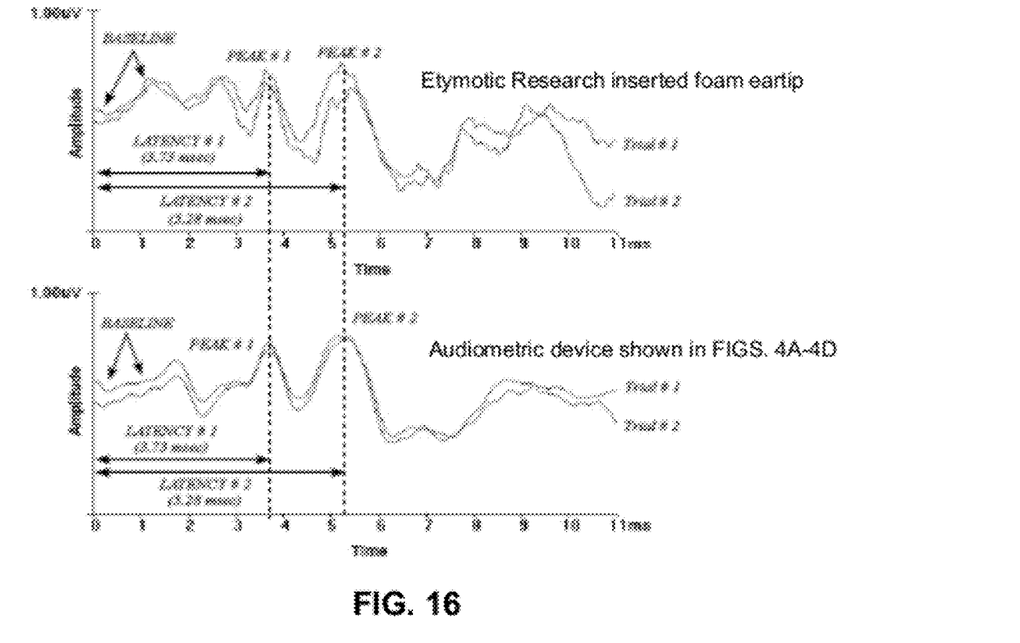
FIG. 16 shows sample ABR recordings acquired using an earphone sound stimulator with both an inserted foam eartip (Etymotic Research) (first graph) and the audiometric device shown in FIGS. 4A-4D (second graph), with some measured time and amplitude parameter values (peaks, latencies, and baseline) marked.
Figure 17:
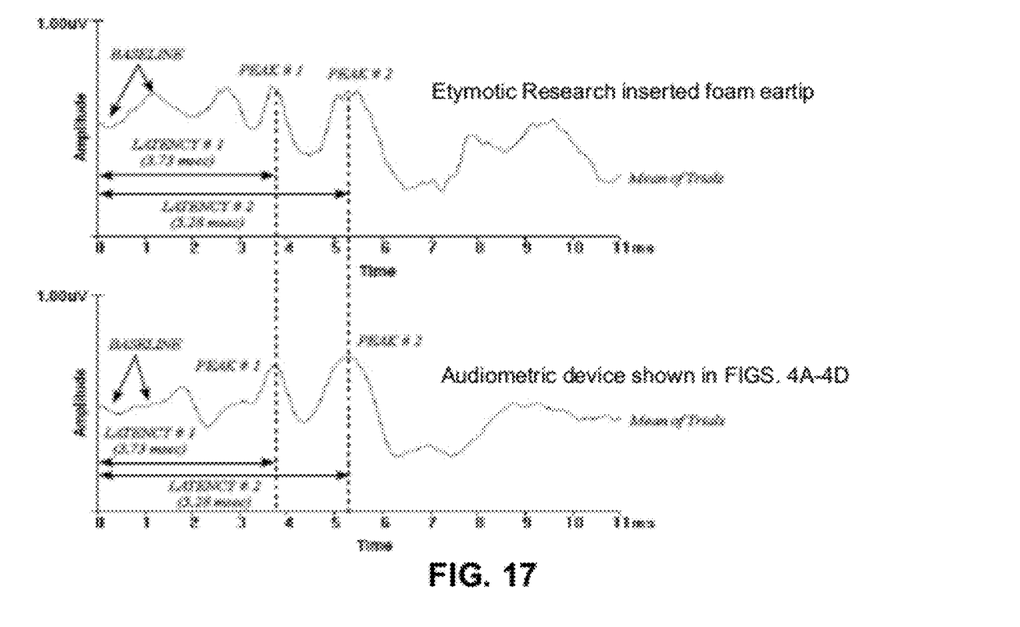
FIG. 17 shows the mean of the two trials of sample ABR recordings acquired using both an inserted foam eartip (Etymotic Research) (first graph) and the audiometric device shown in FIGS. 4A-4D (second graph), with some measured time and amplitude parameter values (peaks, latencies, and baseline) marked.

FIG. 14 displays graphs of the sample ABR recordings acquired using the earphone sound stimulator with both a common inserted foam eartip (shown in the top graph) and the audiometric device of FIGS. 4A-4D (shown in the bottom graph). Both sets of recordings show a high level of repeatability in the resulting acquired waveforms for each trial. FIG. 15 displays the mean of the two sets of ABR recordings for each type of ear coupling device used. There is much similarity in the shapes of both sets of these calculated mean ABR recordings. FIG. 16 displays the two sets of ABR recordings for each type of ear coupling device used along with some measured time and amplitude parameter values marked (as shown, peaks, latencies, and baseline). FIG. 17 displays the mean of the ABR recordings with the same measured time and amplitude parameter values marked. These graphs show that there is a large degree of agreement and matching between the amplitudes and latencies of various peaks of the recordings.

All references, such as patents, patent applications, and publications, referred to above are incorporated by reference in their entirety.

Other embodiments are within the scope of the following claims.

What is claimed is:

1. An audiometric device, comprising:
a substantially flat flexible body from which a protruding portion extends, wherein:
   a) the body and protruding portion each have an average width, wherein the average width (W) of the body is longer than the average width (W1) of the protruding portion:
   b) the body is dimensioned and constructed to substantially adhere to a patient's external ear surface;
   c) the protruding portion has a channel therein extending from the body's side that contacts the patient's external ear surface and the body's other side; and
an adhesive on at least a portion of the body side that contacts the patient's external ear surface, to achieve adherence of the device to the patient's external ear surface.

2. The device of claim 1, wherein the flexible body is generally circular.

3. The device of claim 1, wherein the protruding portion and the flexible body comprise different compositions.

4. The device of claim 1, wherein the protruding portion is harder than the flexible body.

5. The device of claim 1, wherein the adhesive substantially covers the portion of the body side that contacts the patient's external ear surface.

6. The device of claim 1, wherein the protruding portion is constructed and arranged to allow a sound delivery device to engage with the channel and to delivery sound to an ear canal.

7. The device of claim 1, wherein the channel is extended in a direction away from the patient's head.

* * * * *